(12) United States Patent
Hunn (10) Patent No.: US 10,089,439 B2
(45) Date of Patent: Oct. 2, 2018

(54) MEDICAL DEVICE WITH CRYPTOSYSTEM AND METHOD OF IMPLEMENTING THE SAME

(71) Applicant: Stryker Sustainability Solutions, Inc., Tempe, AZ (US)

(72) Inventor: David Robert Joseph Hunn, Mesa, AZ (US)

(73) Assignee: Stryker Sustainability Solutions, Inc., Tempe, AZ (US)

( * ) Notice: Subject to any disclaimer, the term of this patent is extended or adjusted under 35 U.S.C. 154(b) by 22 days.

(21) Appl. No.: 14/925,307

(22) Filed: Oct. 28, 2015

(65) Prior Publication Data
US 2016/0117449 A1    Apr. 28, 2016

Related U.S. Application Data

(60) Provisional application No. 62/069,526, filed on Oct. 28, 2014.

(51) Int. Cl.
| | |
|---|---|
| *G06F 21/62* | (2013.01) |
| *G06F 19/00* | (2018.01) |
| *H04L 29/06* | (2006.01) |
| *G06F 21/64* | (2013.01) |
| *G16H 10/60* | (2018.01) |
| *A61B 5/00* | (2006.01) |

(52) U.S. Cl.
CPC ............ *G06F 19/322* (2013.01); *G06F 21/62* (2013.01); *G06F 21/64* (2013.01); *G16H 10/60* (2018.01); *H04L 63/068* (2013.01); *A61B 5/00* (2013.01); *G06F 2221/2107* (2013.01)

(58) Field of Classification Search
None
See application file for complete search history.

(56) References Cited

U.S. PATENT DOCUMENTS

| | | | | |
|---|---|---|---|---|
| 5,720,293 A | * | 2/1998 | Quinn .................... | A61B 5/028 600/505 |
| 6,266,551 B1 | * | 7/2001 | Osadchy ............ | A61B 1/00059 600/424 |

(Continued)

FOREIGN PATENT DOCUMENTS

| | | |
|---|---|---|
| EP | 1253744 A2 | 10/2002 |
| EP | 1594249 A1 | 11/2005 |

(Continued)

OTHER PUBLICATIONS

Schneier et al.; Secure Audit Logs to Support Computer Forensics; 1999; Retrieved from the Internet <URL: http://dl.acm.org/citation.cfm?id=317089>; pp. 1-18 as printed.*

*Primary Examiner* — Saleh Najjar
*Assistant Examiner* — Michael W Chao
(74) *Attorney, Agent, or Firm* — Howard & Howard Attorneys PLLC (57) ABSTRACT

A medical device and a method of implementing a cryptosystem on the medical device include storing a data structure on a memory component of the medical device. An encryption key is stored in the data structure. Usage data related to usage of the medical device is provided. The encryption key is read from the data structure. The usage data is encrypted with the read encryption key. The encryption key is eliminated such that the encryption key is no longer present in the medical device.

28 Claims, 8 Drawing Sheets

(56) References Cited

U.S. PATENT DOCUMENTS

| | | | | |
|---|---|---|---|---|
| 6,298,255 B1* | 10/2001 | Cordero | A61B 5/04085 | 600/372 |
| 6,308,089 B1* | 10/2001 | von der Ruhr | A61B 5/00 | 600/338 |
| 6,387,092 B1* | 5/2002 | Burnside | A61B 18/14 | 606/32 |
| 7,048,687 B1* | 5/2006 | Reuss | A61B 5/00 | 600/300 |
| 7,240,208 B1* | 7/2007 | Oakley | H04L 9/0897 | 348/207.99 |
| 7,552,340 B2* | 6/2009 | Ooi | G06F 21/78 | 713/186 |
| 8,200,320 B2* | 6/2012 | Kovacs | A61B 5/0205 | 600/513 |
| 8,255,026 B1* | 8/2012 | Al-Ali | A61B 5/14551 | 600/310 |
| 8,684,900 B2* | 4/2014 | Tran | A61B 8/488 | 600/3 |
| 8,700,351 B2* | 4/2014 | Prestidge | G01B 5/012 | 33/1 CC |
| 9,489,785 B2 | 11/2016 | Klammer et al. | | |
| 2004/0078219 A1* | 4/2004 | Kaylor | G06F 19/3418 | 705/2 |
| 2005/0188196 A1* | 8/2005 | Kakii | H04L 9/3263 | 713/156 |
| 2005/0204164 A1* | 9/2005 | Kakii | H04L 9/3268 | 726/5 |
| 2005/0283198 A1* | 12/2005 | Haubrich | G06F 19/3418 | 607/30 |
| 2006/0161054 A1* | 7/2006 | Reuss | A61B 5/00 | 600/300 |
| 2007/0006322 A1* | 1/2007 | Karimzadeh | G06F 19/323 | 726/27 |
| 2007/0185545 A1* | 8/2007 | Duke | A61N 1/3925 | 607/59 |
| 2007/0277836 A1* | 12/2007 | Longley | A61F 5/566 | 128/848 |
| 2008/0097550 A1* | 4/2008 | Dicks | A61N 1/37282 | 607/59 |
| 2008/0288029 A1* | 11/2008 | Healy | A61N 1/37252 | 607/60 |
| 2009/0060287 A1* | 3/2009 | Hyde | A61B 5/0002 | 382/118 |
| 2010/0217987 A1* | 8/2010 | Shevade | G06F 21/6272 | 713/175 |
| 2010/0292556 A1* | 11/2010 | Golden | A61B 5/7465 | 600/364 |
| 2014/0300490 A1* | 10/2014 | Kotz | A61B 5/0028 | 340/870.3 |

FOREIGN PATENT DOCUMENTS

| | | |
|---|---|---|
| EP | 2189922 A2 | 12/2005 |
| WO | WO2006015182 A2 | 2/2006 |
| WO | WO2006020426 A2 | 2/2006 |
| WO | WO2007001328 A2 | 1/2007 |

* cited by examiner

MEDICAL DEVICE WITH CRYPTOSYSTEM AND METHOD OF IMPLEMENTING THE SAME

CROSS-REFERENCE TO RELATED APPLICATIONS

This application claims benefit of U.S. Provisional Patent Application No. 62/069,526, filed on Oct. 28, 2014, the entirety of which is hereby incorporated herein by reference.

TECHNICAL FIELD

The subject invention relates to a medical device, and more specifically, a cryptosystem for a medical device and methods of implementing the same.

BACKGROUND

Conventionally, a medical device, such as a medical probe, is configured to connect to a console. The console and the medical device communicate information back and forth to one another. The medical device often includes a memory that stores data related to the usage of the medical device. For example, such data may denote how many times the medical device has been used.

The stored usage data is important to the operation of the medical device. To ensure consistent performance, the appropriate usage data is read from the memory of the medical device to ensure that the medical device does not operate beyond the intended life span before reprocessing. Those attempting to reprocess or refurbish the medical device for additional use may hack into the medical device and alter the usage data written to the memory. As such, preserving the integrity of the usage data stored in the medical device is important.

SUMMARY

In one embodiment, a medical device is configured to connect to a console. The medical device includes a handpiece. A memory component is positioned in the handpiece. A data structure is stored on the memory component. A plurality of encryption keys are stored in the data structure.

In another embodiment, a medical device including a handpiece is configured to connect to a console. The medical device includes a memory component positioned in the handpiece. A data structure is stored on the memory component and defines an array. A plurality of data segments is contiguously arranged in the array of the data structure. Each of a plurality of encryption keys is stored in one of the data segments. Each of a plurality of decryption keys is associated with one of the plurality of encryption keys. Each decryption key is stored in the same data segment as the associated encryption key. One of the plurality of data segments includes identification data related to the medical device. The decryption keys and the identification data are encrypted.

In yet another embodiment, a used medical device includes a handpiece and is configured to connect to a console. The used medical device includes a memory component positioned in the handpiece. A data structure is stored on the memory component. Encrypted usage data related to usage of the medical device is written to the data structure. The encrypted usage data is encrypted by an encryption key that was previously stored in the data structure and subsequently eliminated such that the encryption key is no longer present in the used medical device.

In one embodiment, a method for manipulating a data structure provided on a memory component of a medical device is provided. The data structure includes an encryption key. The method includes providing usage data related to usage of the medical device. The encryption key is read from the data structure. The usage data is encrypted with the read encryption key. The encryption key is eliminated from the data structure such that the encryption key is no longer present in the medical device.

In yet another embodiment, a method of managing the ability of a control unit to modify authentic usage data on a memory component of a medical device is provided. The memory component includes a data structure with an encryption key. The encryption key is read from the data structure with the control unit. The usage data is encrypted with the encryption key such that the usage data remains authentic. The encrypted usage data is written to the data structure with the control unit. The encryption key is eliminated from the data structure such that the control unit is no longer able to read the encryption key from the medical device thereby preventing the control unit from modifying the authentic encrypted usage data.

The medical device and method advantageously protect the usage data from those attempting to alter the usage data in order to refurbish, reprocess, or otherwise tamper, with the medical device. Eliminating the encryption key provides write-once capability to the memory component. The method provides such capability on various types of memory components, including memory components having standard, unprotected, memory hardware. The method eliminates the need for special, hardware-based, write-once memory protection devices, which can be expensive and limited in application. As such, the medical device and method provide a cost-effective and versatile means to protect the usage data.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Referring to the Figures, wherein like numerals indicate like or corresponding parts throughout the several views, a medical device 10 is generally shown. The medical device 10 is utilized during a medical procedure on a patient. As described throughout, a method is provided for providing write-once capability to a memory component of the medical device 10.

Figure 1:
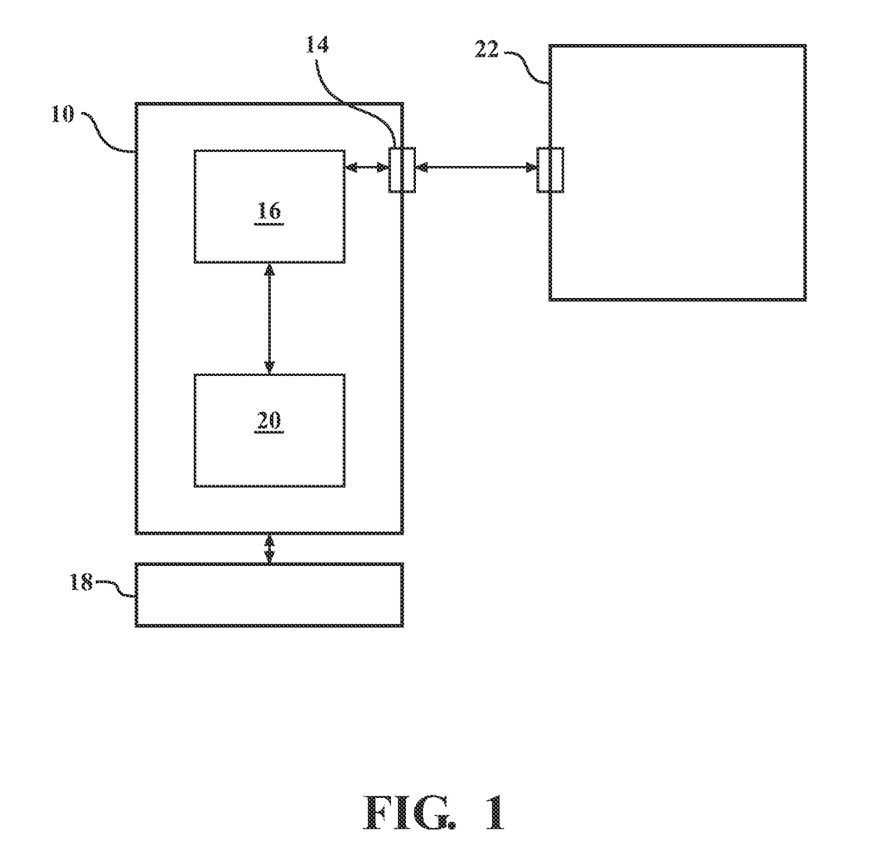
FIG. 1 is a block diagram of the medical device and control unit.

The medical device 10 may have various configurations. In one embodiment, as shown in FIG. 1, the medical device 10 may include a communication port 14 for facilitating communication to and from the medical device 10. A controller 16, such as a microprocessor, may be included in the medical device 10 and connected to the communication port 14. The medical device is configured to be held by a user during use.

Figure 9:
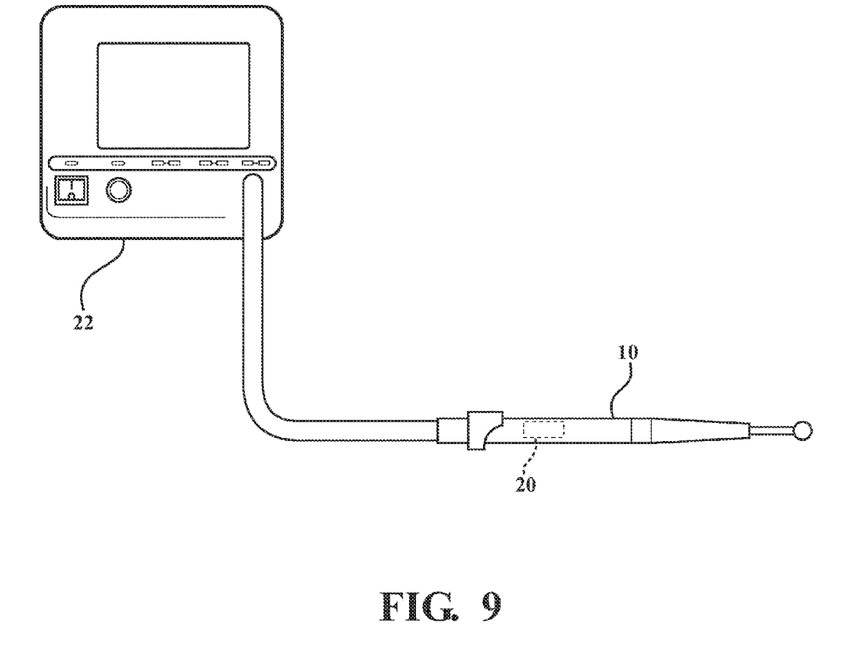
FIG. 9 is an illustration of one example of the medical device and console.

The medical device 10 includes a handpiece. One example of a handpiece is illustrated in FIG. 9. At least a portion of the handpiece can be engaged by a user's hand. Various handpiece configurations are contemplated, including, but not limited to, pistol-type handpieces. The handpiece can include one or more housing components and can be of various sizes and shapes so long as a portion of the handpiece can be engaged by a user's hand.

The medical device 10 may connect to an accessory 18. Examples of the accessory 18 include an end-effector or a sensor. The accessory 18 may be integrated into the medical device 10 or removably attached to the medical device 10. The medical device 10 may be a laparoscopic device, such as sealers or dissectors; a catheter, or a utility tool, such as a burr. The medical device 10 may also be a medical tool.

The medical device 10 includes a memory component 20. The memory component 20 may be disposed in the medical device 10. Furthermore, the memory component 20 may be removable from the medical device 10. Alternatively, the memory component 20 may be an embedded component in the medical device 10. The memory component 20 is in communication with the controller 16. In certain embodiments, the memory component 20 is positioned in the handpiece. In other words, the memory component 20 may be within or adjacent to the housing associated with the handpiece. The memory component 20 may be connected to a circuit board positioned in the handpiece.

The memory component 20 may include any suitable readable and writable data medium for storing data. The memory component may be non-transitory. For example, the memory component 20 may be a random access memory (RAM). The memory component 20 may be a standalone memory device, such as a standalone memory card or flash card. Alternatively, the memory component 20 may be a sub-component of the controller 16.

In one embodiment, the memory component 20 is a standard, unprotected memory component. Said differently, in such an embodiment, the memory component 20 is implemented in non-secure, memory hardware. In such instances, the memory component 20 is unprotected by a hardware-level, access control in which the ability to access the memory component 20 is constrained by hardware-level implementations. The memory component 20 may be entirely disconnected, or free from, the hardware-level access control. Alternatively, the memory component 20 may be connected to hardware-level access control. The hardware-level access control may be deactivated. Examples of hardware-level access control include mandatory access control (MAC), discretionary access control (DAC), and the like.

The medical device 10 is configured to connect to a console 22. The medical device 10 and console 22 are typically physically separate components. In other words, the medical device may be held in the hand of a user, while the console 22 is disposed on a table top. One example of the console 22 is illustrated in FIG. 9. The console 22 may include any suitable interface, such as visual or tactile interfaces, for enabling an operator to interface with the console 22. Additionally, the console 22 may include a memory that is separate from the memory component 20 in the medical device 10.

The console 22 is configured to communicate with the medical device 10, and vice-versa. More specifically, the console 22 is configured to communicate with the controller 16 and/or memory component 20 of the medical device 10. The medical device 10 and the console 22 may communicate according to any suitable method. The medical device 10 and console 22 communicate bi-directionally such that the medical device 10 receives and sends communications. The medical device 10 may communicate with the console 22 by an electrical cable, wirelessly, or by other means. In one embodiment, the cable connects from the console 22 to the medical device 10, such as the communication port 14. The console 22 may communicate with the medical device 10 to control the medical device 10 before, during, or after, a medical procedure or surgical operation. The console 22 may also provide power or energy to the medical device 10.

The console 22 may send memory commands for controlling the memory component 20 of the medical device. For example, the console 22 may send a command to read data from and/or write data to the medical device 10, as is described in detail below.

Figure 2:
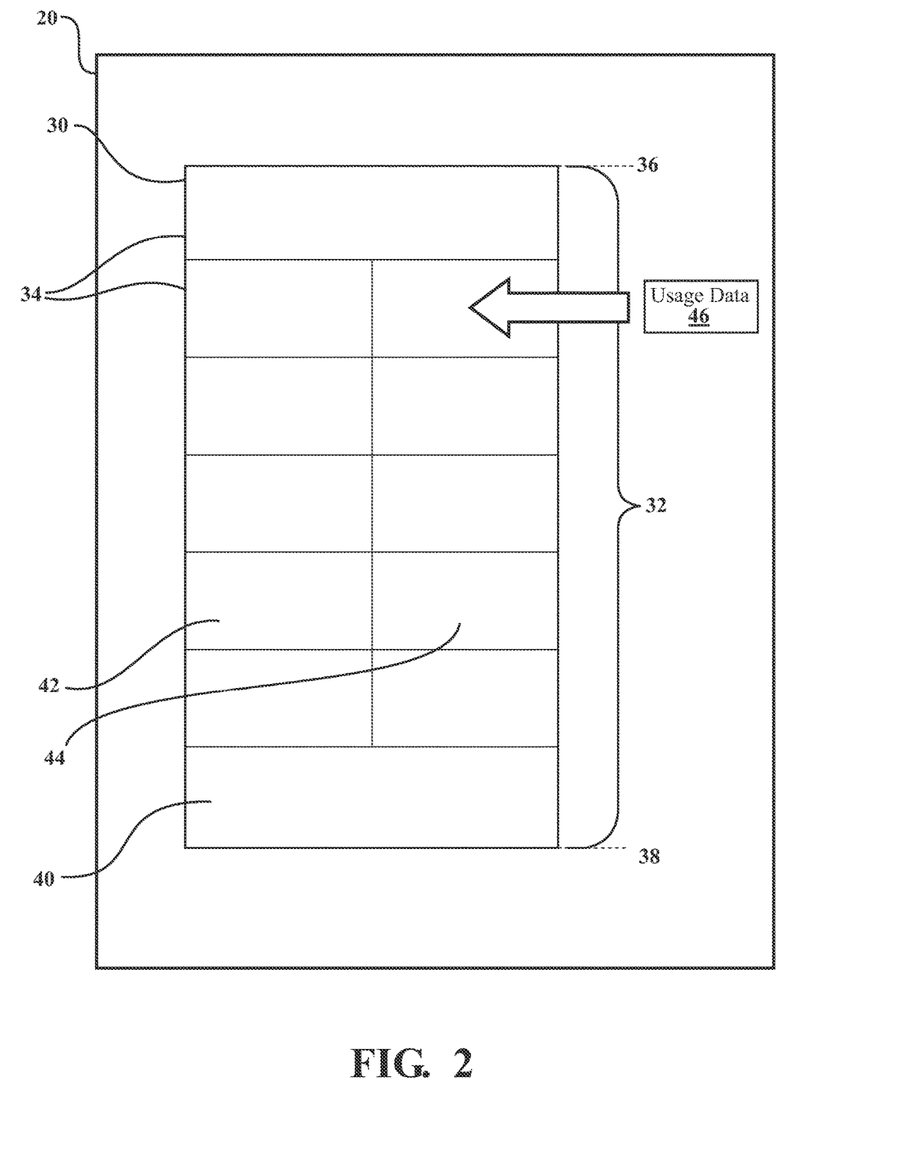
FIG. 2 illustrates an embodiment of a memory component of the medical device.

As shown in FIG. 2, the memory component 20 of the medical device 10 includes a data structure 30. The data structure 30 is stored on the memory component 20. The data structure 30 may include any suitable configuration or scheme for organizing data in the memory component 20.

In one embodiment, the data structure 30 includes an array 32. The array 32 may be finite and occupy the memory component 20 between a starting position 36 defining the beginning of the array and an ending position 38 defining the end of the array 32.

The data structure 30 may be sized and configured to occupy the memory component 20 completely. For example, the data structure 30 may be of a fixed size to occupy the memory component 20 completely. Alternatively, the data structure 30 may be expandable or scalable such that the data structure 30 completely occupies the memory component 20. The advantages of expanding or scaling the data structure 30 to match the capacity of the memory component 20 are described in detail below.

The data structure 30 often includes a data segment 34. In one embodiment, the data structure 30 includes a single data segment 34. Alternatively, as shown in FIG. 2, the data structure 30 may include a plurality of data segments 34. The data structure 30 may include any suitable number of data segments 34 necessary for compatibility with the operation of the medical device 10. The data segment(s) 34 may occupy a portion of virtual address space in the memory component 20. As is described in detail below, the data segment(s) 34 is configured to store data, such as usage data or calibration data. The data segment(s) 34 may have any suitable size. In instances where there is a plurality of data segments 34, each of the data segments 34 may have the same size. Any suitable method may be utilized to determine which data segment(s) 34 are to be accessed and when such data segment(s) 34 should be accessed. The data segment(s) 34 may each be identified by an array index, integer, or key.

The data segment(s) 34 are arranged in the data structure 30. More specifically, the data segment(s) 34 are arranged in the array 32. The data segment(s) 34 are arranged between the starting position 36 and ending position 38 of the array 32. The array 32 facilitates quick and random access to the data segments 34. The data segment(s) 34 may be arranged randomly or according to a specified order. Furthermore, the data segment(s) 34 may be arranged contiguously. For example, the data segments 34 may be arranged end-to-end with no virtual space between adjacent data segments 34 such that the data segment(s) 34 completely occupy the virtual space of the memory component 20 between the starting position 36 and ending position 38 of the array 32.

Each data segment(s) 34 may include an undivided single portion 40 for storing data. Alternatively, each data segment(s) 34 may be divided into more than one portion 40 for storing data. For example, the data segment(s) 34 may be divided into a first portion 42 and a second portion 44 that is contiguous to the first portion 42. The first and second portions 42, 44 may be arranged virtually side-by-side. Optionally, the data segment(s) 34 may include an additional blank memory area for increasing the usable data density of the memory component 20. Alternatively, the data segment(s) 34 may exclude the additional blank memory area. The data structure 30 may include any combination of divided and undivided data segments 34.

The memory component 20 is configured to store usage data 46, calibration data, or other data related to the operation of the medical device 10 or console 22. The usage data 46 provides information related to usage of the medical device 10. In one example, the usage data 46 represents how many times the medical device 10 has been used. In another example, the usage data 46 represents a predefined shelf-life of the medical device 10. The usage data 46 may represent how long the medical device 10 has been used. In yet another example, the usage data 46 represents compatibility of the medical device 10. Compatibility may be determined with respect to the accessory 18, the console 22, and/or a patient. The usage data 46 may represent a combination of information from the aforementioned examples. The usage data 46 may vary depending on what type of medical device is being used. For example, the usage data 46 may include speed of rotation, temperature, usage time, time of first use, and other parameters. Additionally or alternatively, the usage data 46 may represent any suitable other information related to usage of the medical device 10 not specifically recited herein.

The memory component 20 may store a plurality of usage data 46. As is described in detail below, the usage data 46 is stored in the data segment 34. The plurality of usage data 46 may be stored in various data segments 34. The usage data 46 may be represented by any suitable format, including, but not limited to a plaintext format. In one embodiment, the usage data 46 is padded to match the size of the available space in the data segment 34. This padding of the usage data may be operable to prevent additional data from being written to the data segment once the padded usage data has been written to that data segment.

The usage data 46 is provided according to various configurations and methods. In one embodiment, the medical device 10 generates the usage data 46. For example, the controller 16 of the medical device 10 may generate the usage data 46. In another embodiment, the console 22 generates the usage data 46. The usage data 46 may be transmitted back and forth between the medical device 10 and the console 22. The usage data 46 may be read from and/or written to, the memory component 20. For example, the console 22 may send a memory command to read the usage data 46 from and/or write the usage data 46 to, the memory component 20.

The usage data 46 may be generated at any suitable time, and before or after any suitable event. Additionally, the usage data 46 may be written to be memory component 20 at any suitable time. The data segment 34 is initially unused. In such instances, there is no usage data 46 in the data segment 34. For example, in such embodiments, the usage data 46 is deliberately not stored into the data segment 34 during manufacturing and/or the initial configuration of the medical device 10 and/or memory component 20. However, the usage data 46 may be written to the data segment 34 after the medical device 10 is first used and thereafter during subsequent uses. Alternatively, the usage data 46 may be initially written to the memory component 20 during manufacturing and/or initial configuration of the medical device 10 and/or memory component 20. In other embodiments, some data segments 34 are used while other data segments 34 are unused before use of the medical device by an end-user. For example, some data segments 34 may initially have usage data 46 stored therein, while others do not. The terms "used" and "unused" with respect to the data segment 34 are intended to refer to the respective presence or absence of usage data 46 in the data segment 34. In this respect, the data segment(s) 34 may be unused but still include information or parameters for implementing cryptographic functions, as described immediately below.

Figure 3:
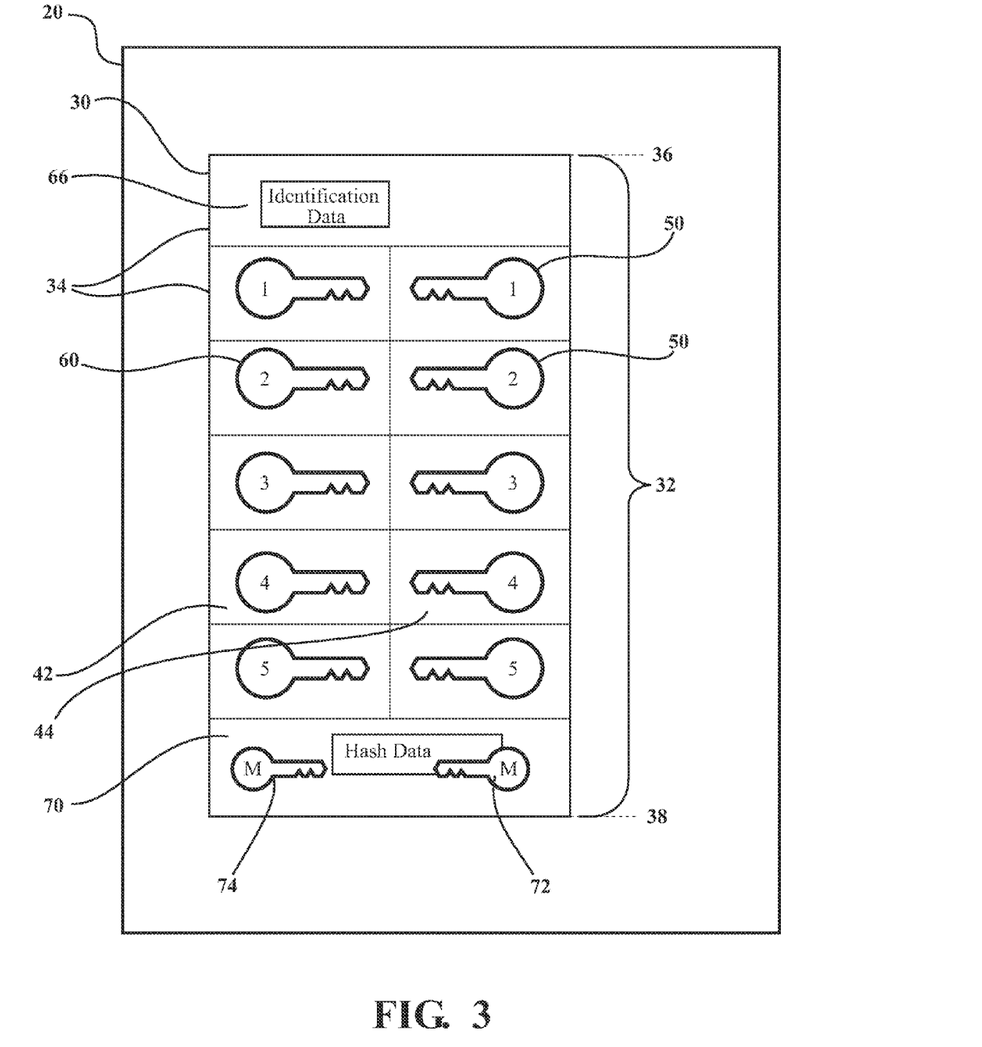
FIG. 3 is a diagram illustrating another embodiment of the memory component of the medical device.
Figure 4:
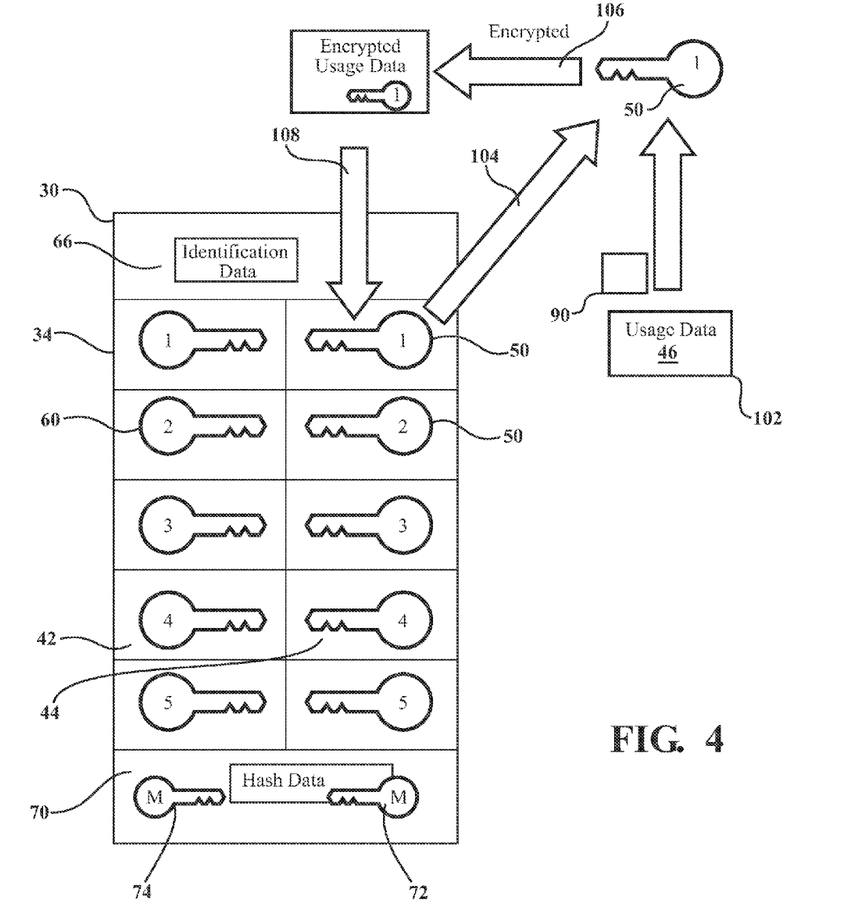
FIG. 4 is a block diagram illustrating manipulation of a data structure of the memory component of FIG. 3.

As shown in FIGS. 3 and 4, the memory component 20 of the medical device 10 includes at least one encryption key 50. Specifically, the encryption key 50 is stored in the data structure 30. In more specific embodiments, the encryption key 50 is stored in a data segment 34. The memory component 20 may include a plurality of encryption keys 50. In FIGS. 3 and 4, the encryption keys 50 are numerically identified 1-5 for simplicity in illustration. However, such numbers are merely provided for simplicity in description and do not limit the scope and/or order of the encryption keys 50. In one instance, each encryption key 50 is stored in one of the data segments 34. In other words, only one encryption key 50 is stored in each data segment 34. Each and every data segment 34 in the data structure 30 may include one encryption key 50. Alternatively, some data segments 34 in the data structure 30 may include one encryption key 50 while other data segments 34 do not include any encryption key(s) 50, as shown in FIG. 3. In instances where the data structure 30 is arranged in the array 32, the encryption keys 50 may be arranged in series, one after another, within contiguous data segments 34. In one example, the encryption keys 50 occupy each of the data segments 34 in the array 32 between the start 36 and end of array 38. Additionally, the encryption key 50 may be stored in a portion 40 of the data segment 34. The encryption key 50 in the data segment 34 is different from the usage data 46 written to the data segment 34.

The encryption key 50 may be randomly generated. In instances where there is a plurality of encryption keys 50, each of encryption keys 50 may be randomly generated such that no two encryption keys 50 are identical. Furthermore, the encryption keys 50 can be stored in the memory component 20 at the time of manufacture of the memory component 20, or thereafter. In some embodiments, the console 22 configured to connect to the medical device 10 does not include any encryption keys.

As shown in FIG. 4, the encryption key 50 is readable from the memory component 20. More specifically, the encryption key 50 is readable from the data segment 34. The encryption key 50 may be read according to any suitable protocol or method. In one embodiment, as shown in FIG. 4, the console 22 reads the encryption key 50. In another embodiment, the controller of the medical device 10 reads the encryption key 50. The encryption key 50 may be read to any suitable location, including any suitable component of the medical device 10 or the console 22. In one embodiment, the encryption key 50 is read such that the encryption key 50 is virtually and physically removed from the memory component 20 after being read. In such instances, the encryption key 50 is not merely copied. This removal results in the encryption key 50 being completely eliminated from any component within the handpiece. Alternatively, the encryption key 50 is read by copying the encryption key 50 from the data segment 34 to one or more locations.

As shown in FIG. 4, the encryption key 50 is configured to encrypt the usage data 46. Generally, the encryption key 50 converts readable plaintext of the usage data 46 into an unreadable encrypted form for maintaining secrecy of the usage data 46. More specifically, the encryption key 50 provides parameters to facilitate transformation of the readable plaintext into unreadable encrypted (cipher) text. The encryption key 50 enables valid or authentic usage data 46 to be preserved in encrypted form. Preservation of the encryption key 50 ensures that the usage data 46 can be verified or authenticated to ensure that the usage data 46 was not tampered with. Thus, if a party does not have an encryption key 50, that party could not write valid usage data 46 that can pass verification.

The usage data 46 is encrypted by the encryption key 50 read from the memory component 20. In one embodiment, encryption of the usage data 46 occurs on the medical device 10. For example, encryption occurs on the memory component 20. Alternatively, encryption of the usage data 46 may occur on the console 22 and/or on any suitable medium between the medical device 10 and the console 22. In other words, the medical device 10 and/or the console 22 may initiate encryption of the usage data 46. Additionally, padding of the usage data 46 may be done before or after encryption.

As shown in FIGS. 3 and 4, at least one decryption key 60 is associated with the encryption key 50. Generally, the decryption key 60 provides parameters to facilitate transformation of the unreadable encrypted text of the usage data 46 back into readable plaintext such that the usage data 46 is comprehensible. Thus, the encrypted usage data can be read with the decryption key 50. The decryption key 60 also provides verification that the usage data 46 is valid. In one embodiment, the decryption key 60 is solely capable of decrypting the usage data 46 encrypted by the associated encryption key 50.

The memory component 20 may include a plurality of decryption keys 60. In FIGS. 3 and 4, the decryption keys 60 are numerically identified 1-5 for simplicity. In instances where there are many encryption keys 50, each of a plurality of decryption keys 60 may be associated with one of the plurality of encryption keys 50. In other words, each decryption key 60 is associated with only one encryption key 50. As such, there are an equal number of encryption keys 50 and decryption keys 60. The decryption keys 60 may be randomly generated such that no two decryption keys 60 are identical. The step of decryption may occur on the medical device 10. Alternatively, the step of decryption may occur on the console 22.

In one embodiment, as shown in FIGS. 3 and 4, the decryption key 60 is stored in the memory component 20 on the medical device 10. More specifically, the decryption key 60 is stored in the data segment 34 of the data structure 30. In instances with a plurality of decryption keys 60, each decryption key 60 is stored in one of the data segments 34, as shown in FIGS. 3 and 4. In other instances, each data segment 34 in the data structure 30 may include one decryption key 60. The data segments 34 may be stored in all of the data segments 34, some of the data segments 34, or none of the data segments 34. Thus, some data segments 34 may not include a decryption key 60.

In FIGS. 3 and 4, for example, each data segment 34 that includes one encryption key 50 further includes one decryption key 60. One or more of the data segments 34 in the memory component 20 may consist only of the associated encryption and decryption keys 50, 60. For example, the decryption key 60 may be stored in the first portion 42 of the data segment 34 and the encryption key 50 may be stored in the second portion 44 of the same data segment 34. Some data segments 34 in the data structure 30 may include one decryption key 60 while other data segments 34 do not include any decryption key(s) 60. In instances where the data structure 30 is arranged in the array 32, the decryption keys 60 may be arranged in series, one after another, within contiguous data segments 34. For example, the decryption keys 60 may occupy each data segment 34 in the array 32 between the start 36 and end of array 38. The decryption key(s) 60 can be stored in the memory component 20 at the time of manufacture of the memory component 20, or thereafter.

In another embodiment, the decryption key 60 is stored somewhere other than in the memory component 20. For example, the decryption key 60 may be stored in the console 22, or, more specifically, the memory of the console 22. A plurality of decryption keys 60 may be stored in the console 22. When this is the case, the memory component 20 of the medical device 10, before use, includes the encryption keys 50, but not the associated decryption keys 60. The encryption keys 50 are stored in the data segments 34 as described above.

The encryption keys 50 and decryption keys 60 may have any suitable configuration based on any combination of the embodiments described herein, and those not specifically recited herein.

Any suitable methods or algorithms may permit transformation of the plaintext of the usage data 46 to encrypted usage data, and vice-versa. In one instance, symmetric-key or private-key encryption methods are utilized. Here, the associated encryption key 50 and decryption key 60 in one data segment 34 are identical. In other words, either one of the encryption or decryption keys 50, 60 can encrypt and/or decrypt the usage data 46. The encryption and decryption keys 50, 60 are kept private before and after writing usage data 46 to ensure security.

In another instance, asymmetric-key or public-key encryption methods may be employed. Here, the associated encryption key 50 and decryption key 60 in one data segment 34 are different. The keys 50, 60 are different in that one is a private key and the other is a public key. The public key is widely disseminated to any party requesting such. The private key is kept private and secure such that it is known only to the parties who are authorized to access the usage data 46. The usage data 46 cannot be decrypted by parties who do not possess the private key. As explained above, when one of the keys 50, 60 in the data segment 34 is used to encrypt the usage data 46, the associated other key from that data segment 34 is required to decrypt the usage data 46. For example, if a first party encrypts the usage data 46 with a public encryption key 50, the associated private decryption key 60 is required to decrypt the usage data 46. The private encryption key 50 may be held by the first party or a second party having authorized access to such. Alternatively, if the first party encrypts the usage data 46 with a private encryption key 50, the associated public decryption key 60 is required to decrypt the usage data 46 thereby demonstrating that the first party, or a second party having access to the private encryption key 50, performed the encryption.

In instances when the decryption keys 60 are stored in the data structure 30, the data structure 30 may also include a unique data segment 66, as shown in FIG. 3. The unique data segment 66 is a data segment 34 in the data structure 30 that includes identification data. The identification data is used for security purposes to prevent unwanted alteration of the usage data 46 within the memory component 20. In one embodiment, the identification data relates to the memory component 20 on which the data structure 30 is stored. For example, the identification data may be a unique serial number or lot number of the memory component 20. Alternatively, the identification data may relate to the medical device 10. For example, the identification data may be an authentication code provided by the medical device 10 or may be calibration information required to operate the medical device 10. Additionally, the identification data may help verify that the usage data 46 belongs to a specific medical device 10 as was not copied off another medical device 10. The identification data may also correspond to characteristics of the medical device 10, and/or accessories of the medical device 10. The identification data may be stored in the unique data segment 66 at the time of manufacture or any suitable time thereafter. The unique data segment 66 may be located at any suitable location in the data structure 30. In one instance, the unique data segment 66 is located at the start 36 of the array 32. Additionally, the unique data segment 66 may occupy an entire, undivided data segment 34, such that no other data may be stored in the data segment which is occupied by the unique data.

In instances when the unique data segment 66 and decryption keys 60 are stored in the data structure 30, the data structure 30 may include a verification data segment 70, as shown in FIG. 3. The verification data segment 70 may be similar to other data segments 34 in the data structure 30. The verification data segment 70 may be located at any suitable location in the data structure 30. In one instance, where the data structure includes the array 32, the verification data segment 70 is located at the end 38 of the array 32. Additionally, the verification data segment 70 may comprise an entire undivided data segment 34.

In one embodiment, the verification data segment 70 includes cryptographic hash data. A hash generator generates the hash data. The hash data may be generated or regenerated at any suitable time or event. For example, the hash data may be regenerated each time the data stored in the data structure 30 changes, or more specifically, whenever usage data 46 is written to the memory unit. Additionally, the hash data may be generated when certain entities, e.g., control units, write usage data 46 to the memory unit 20. In one example, the hash generator receives, as an input, the values of the unique data segment 66 and the decryption keys 60 in the data structure 30. The hash generator converts, or maps, the inputted values into hash data (a digest), which is significantly different from the originally inputted values. For security purposes, the hash data is practically impossible to invert back to the originally inputted values. However, the hash data provides verification of usage data 46 integrity.

The hash data is compared to determine whether any changes exist to usage data 46 written to one of the data segments 34. To illustrate, the hash data may be generated initially after writing usage data 46 to one of the data segments 34. To verify that the usage data 46 has not been manipulated by an unauthorized user, the hash data is subsequently generated at a later time, for example, when the usage data 46 is read from the memory component 20. The initially generated hash data is compared to the subsequently generated hash data. If the comparison reveals no difference in the hash data, then the usage data 46 can be authenticated as unmodified. If the comparison reveals a difference between the initially generated hash data and the subsequently generated hash data, the medical device 10 or console 22 prevents writing to memory unit 20. The underlying inputted values remains guarded.

The hash data may be generated and compared before or after any suitable event. Additionally, the hash generator may be executed on the medical device 10 or the console 22. The hash generator may operate according to any suitable function or algorithm, including, but not limited to a Secure Hash Algorithm (SHA), Message-Digest Algorithm (MD), and the like.

The hash data may be encrypted by a master encryption key 72. In one embodiment, the master encryption key 72 provides access to the encrypted hash data that is stored in the verification data segment 70. The hash data may be stored in the verification data segment 70 before encryption or after. The encrypted hash data may be stored in the verification data segment 70 at the time of manufacture of the memory component 20 or any suitable time thereafter. The master encryption key 72 may be implemented according to any suitable method. The hash data may be encrypted at any suitable time during or after its generation. In one embodiment, the master encryption key 72 is generated by asymmetric key encryption techniques.

The encrypted hash data is decryptable by a master decryption key 74 associated with the master encryption key 72. The master decryption key 74 may be stored on the medical device 10, the console 22, or any suitable medium between the medical device 10 and the console 22. As shown in FIG. 3, the master decryption key 74 may also be stored in the memory component 20. In one embodiment, the master decryption key 74 is generated by asymmetric key encryption techniques.

The master decryption key 74 may permit read access to the entire data structure 30. More particularly, the master decryption key 74 allows decryption of the encrypted hash data in the verification data segment 70 such that the hash data is comprehensible. The master decryption key 74 allows the console 22, control unit 12, or other device access to the hash data for checking integrity and/or validity of the hash data. With the decrypted hash data, the master decryption key 72 provides access to read and verify the integrity and/or validity of the data and keys written to the data structure 30. In one example, the master decryption key 74 allows the console 22, control unit 12, or other device to confirm that the decrypted hash data matches the identification data in the unique data segment 66 and matches decryption key(s) 60. The master decryption key 74 may also permit console 22, control unit 15, or other device to confirm that the identification data in the unique data segment 66 matches the device characteristics, serial numbers, or other independent data sources that were originally inputted. Additionally, the master decryption key 74 may allow each data segment 34 in the data structure 30 to be checked to ensure that each decryption key 60 matches the associated encryption key 50.

In another embodiment, the decryption keys 60 and identification data are protected using asymmetric key encryption utilizing the master encryption key 70 and the master decryption key 72. Here, the master encryption key 70 is a secret key and the master decryption key 72 is a public key. Only certain consoles 22 have access to the secret key, while certain other consoles 22 have access to the public key. Similar methods may be employed with respect to the usage data 46 and encryption keys 50. Specifically, the usage data 46 and the encryption keys 50 may be protected using asymmetric key encryption wherein the master encryption key 70 is a secret key and the master decryption key 72 is a public key. Only certain consoles 22 have access to the secret key, while certain other consoles 22 have access to the public key.

Accordingly, embodiments of the data structure 30 including the unique data segment 66, the verification data segment 70, and the master encryption and decryption keys 72, 74 provide added security to prevent unauthorized duplication of the data structure 30. Mainly, copying the data structure 30, when the information in the data structure is encrypted or encoded as hash data, would yield incomprehensible text because the master decryption key 74 is needed to gain read-access to the data stored in data structure 30. Additionally, such configurations permit a hierarchy access to the data stored in the data structure 30 such that access by one entity to the data structure 30, such as write-once access, does not cause insecurity to others entities accessing the data structure 30. Furthermore, the master encryption and decryption keys 72, 74 prevent attackers from changing the decryption keys 60 on the medical device 10.

In addition to any of the aforementioned embodiments, the medical device 10 and/or console 22 may further employ any suitable algorithm for checking the integrity of the usage data 46 transmitted between the medical device 10 and the console 22. As shown in FIG. 4, a cyclic redundancy check (CRC) 90 is employed for detecting changes to the usage data 46. The CRC 90 may also help facilitate encryption of the usage data 46 with the encryption key 50.

Figure 5:
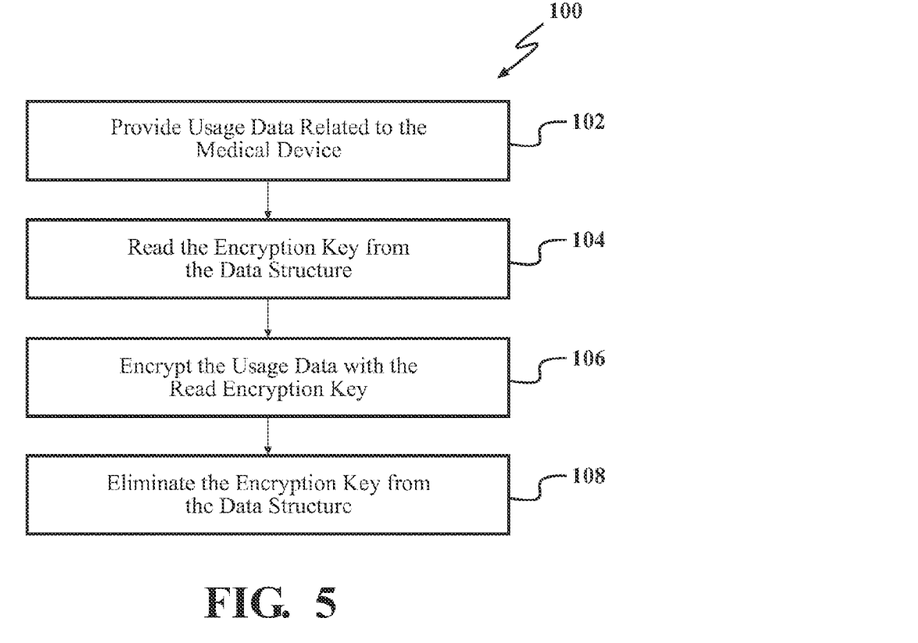
FIG. 5 is a flow chart of a method of providing write-once capability to the memory component.

The method for providing write-once capability to the memory component 20 of the medical device 10 is illustrated in FIG. 4 and identified by numeral 100 in FIG. 5. At step 102, the usage data 46 related to usage of the medical device 10 is provided. At step 104, the encryption key 50 is read from the memory component 20 of the medical device 10. The usage data 46 is encrypted with the read encryption key 50 at step 106.

At step 108, the method includes eliminating the encryption key 50. As described, the usage data 46 is encrypted by the encryption key 50 that is stored in the data segment 34. The encryption key 50 in that particular data segment 34 is eliminated.

The medical device 10, the console 22, or any other medium between the medical device 10 and console 22, may provide and/or initiate elimination of the encryption key 50. The encryption key 50 may be eliminated according to any suitable method. Additionally, the encryption key 50 may be eliminated at any suitable time or event. For example, the encryption key 50 may be eliminated immediately after the usage data 46 is encrypted and/or upon execution of a command.

Figure 6:
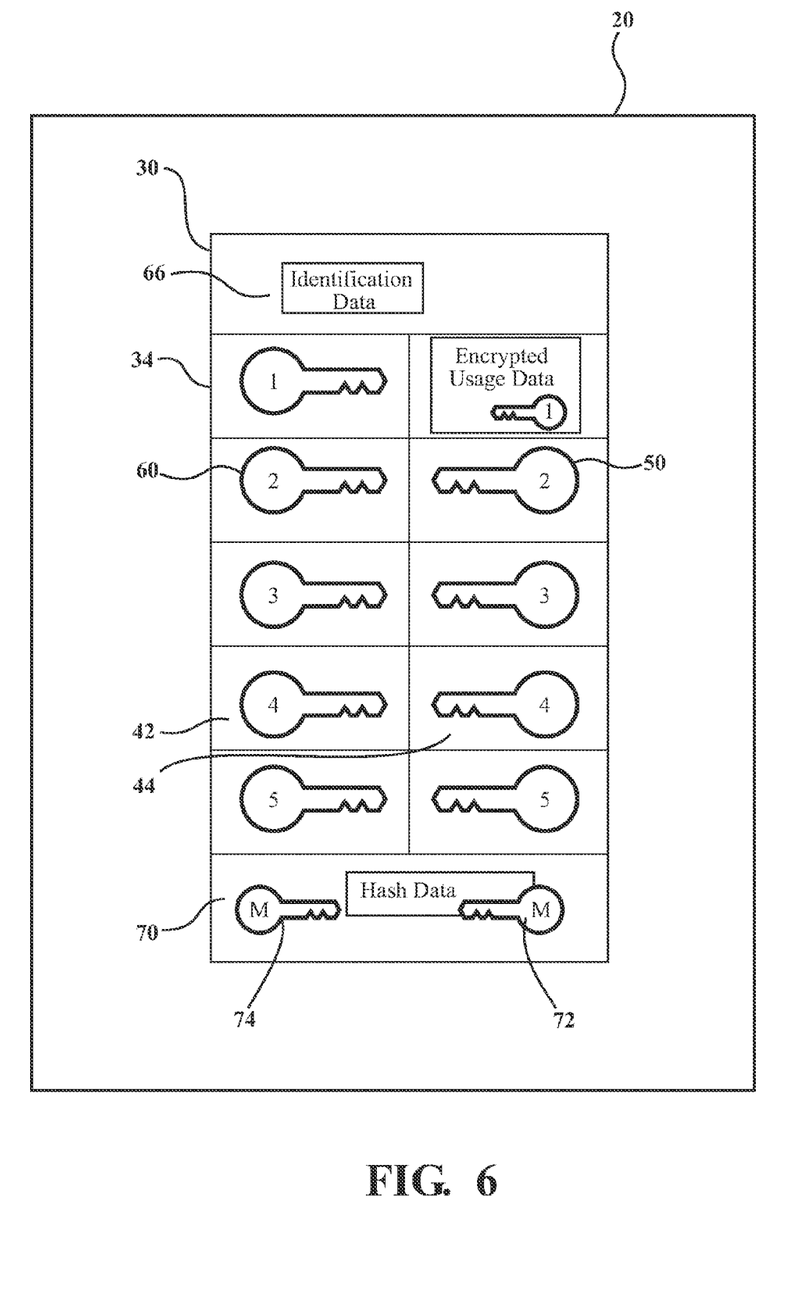
FIG. 6 is a diagram illustrating the data structure of the memory component of FIG. 4 after manipulation in accordance with one embodiment.

Eliminating the encryption key 50 from the data structure 30 also eliminates the encryption key 50 from the data segment 34, as shown in FIG. 6. By eliminating the encryption key 50, the encryption key 50 is no longer stored in the data segment 34 or readable from the memory component 20. That is, neither the medical device 10 nor the console 22 can read the encryption key 50 from any location after the encryption key 50 is eliminated. In other words, the encryption key 50 is erased from the memory component 20. Eliminating the encryption key 50 ensures that no new encrypted data can be written with the eliminated encryption key 50. As will be described in detail below, the encryption key 50 may be unreadable for certain entities having write-once access to the memory component 20, while still being readable by certain entities having full write access.

Eliminating the encryption key 50 prohibits subsequent writing of authentic usage data 46 to the memory component 20. More specifically, eliminating the encryption key 50 from the data segment 34 in which the encryption key 50 was originally stored prohibits subsequent writing of the usage data 46 to that particular data segment 34. In other words, because the encryption 50 is no longer available for association with the usage data 46, the usage data 46 is no longer capable of being written to the data segment 34. Eliminating the encryption key 50 eliminates the capability of subsequently writing valid or authentic usage data 46 to the data segment 34. Said differently, the usage data 46 linked to the encryption key 50 can only be written once to the memory component 20 because a party having only write-once access privileges has no other way of accessing the encryption key 50.

In one embodiment, the encryption key 50 is eliminated by being overwritten by the encrypted usage data. In other words, the encrypted usage data is written to the same data segment 34 in which the encryption key 50 was stored. Said differently, the encrypted usage data is stored in the memory component 20 in the same location that the encryption key 50 had occupied. Overwriting the encryption key 50 with the encrypted usage data causes the data segment 34 to be used in instances where the data segment 34 is unused prior to overwriting. In some instances, the encryption key 50 may be overwritten multiple times to ensure that the encryption key 50 is no longer recoverable from the medium.

As described above, the data structure 30 may be configured to occupy the memory component 20 completely. As such, in this embodiment, there exists no blank data area in the data structure 30. By completely occupying the memory component 20, the encrypted usage data is forced to be written to the data structure 30. More specifically, the encrypted usage data must overwrite the encryption key 50, as there exists nowhere else to in the data structure 30 to store the encrypted usage data. This prevents an entity from re-saving the encryption key 50 in a blank data area, which ensures that the encryption key 50 is destroyed, i.e., eliminated, from the memory component 20 when the usage data 46 is written.

The method 100 provides write-once capability to the memory component 20 of the medical device 10. The method 100 advantageously allows such capability to be employed on various types of memory components 20, including memory components 20 having standard, unprotected memory hardware. The method 100 eliminates the need for special hardware-based, write-once memory protection devices, which can be expensive and limited in application.

Figure 7:
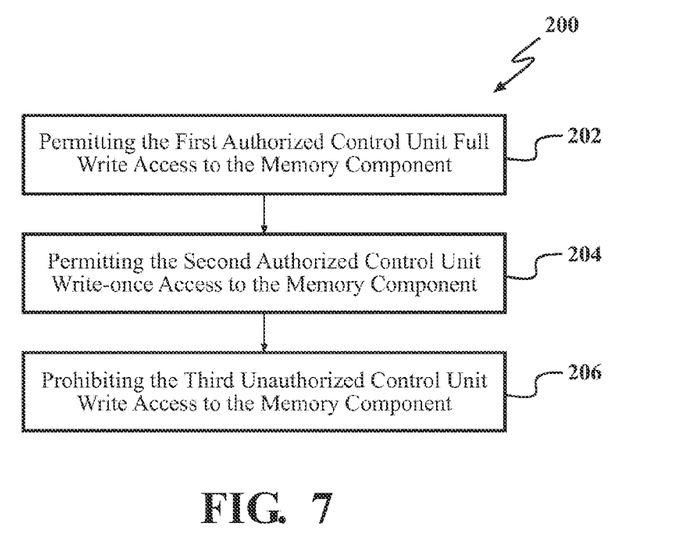
FIG. 7 is a flow chart of one embodiment of a method of managing the ability of control units to write encrypted usage data from and to the memory component.
Figure 8:
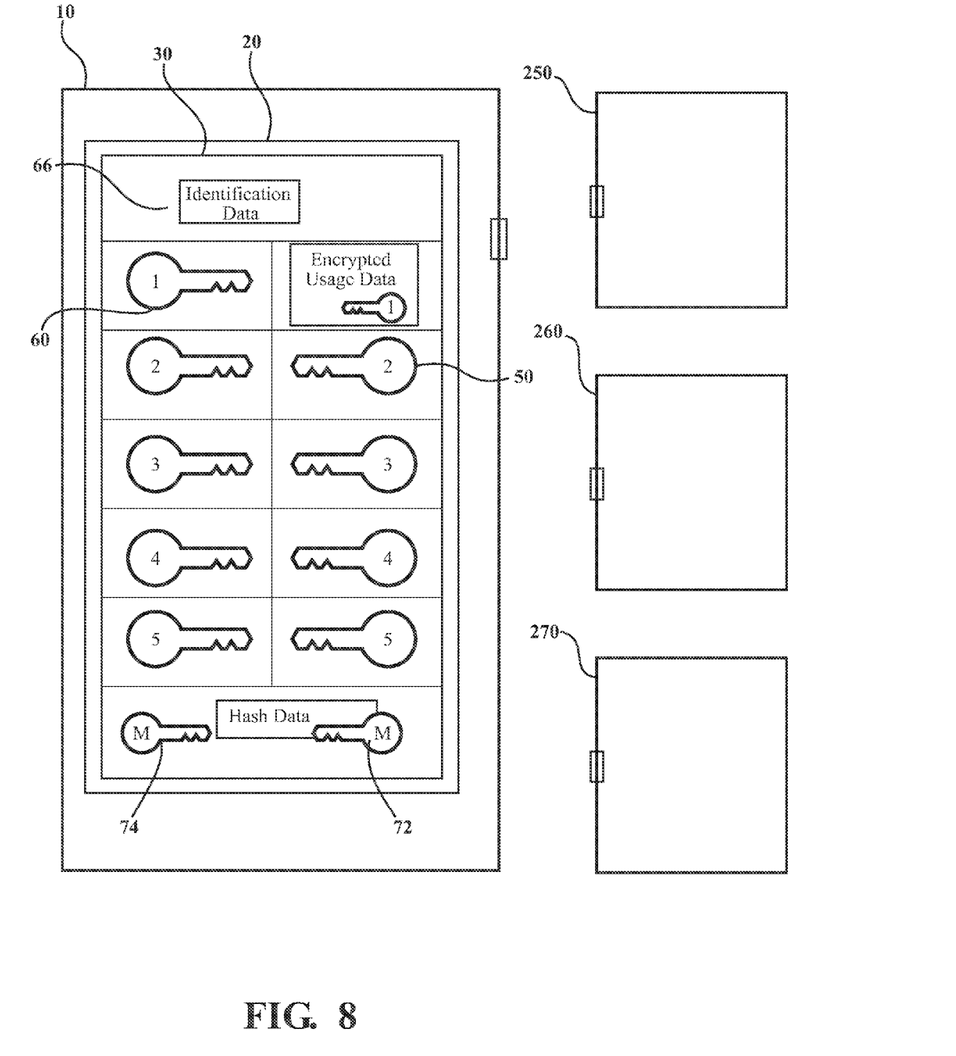
FIG. 8 is a diagram illustrating the medical device and a plurality of control units having various levels of authorization to read and write encrypted usage data from and to the memory component.

A method of managing read and write access to the memory component 20 of the medical device 10 is provided at 200 in FIG. 7. The method 200 provides managing read and write access between a first authorized control unit 250 and a second authorized control unit 260, which are illustrated in FIG. 8. The first authorized control unit 250 has a first level of access. The second authorized control unit 260 has a second level of access that is more restricted than the first level of access. The method 200 may optionally manage read and write access between the first authorized control unit 250, the second authorized control unit 260, and a third unauthorized control unit 270. The third unauthorized control unit 270 is shown in FIG. 8. The control units 250, 260, 270 may have the same or different configuration as the console 22 described herein. Any of the control units 250, 260, 270 may be connected to the medical device 10 simultaneously or at different times.

In one example, the first authorized control unit 250 is controlled by an original manufacturer or master administrator. The second authorized control unit 260 is controlled by a consumer, such as a hospital, practitioner, and the like. The third unauthorized control unit 270 is controlled by an entity attempting to refurbish or reprocess the medical device 10. For example, such an entity may connect the third unauthorized control unit 270 to the medical device 10 in an attempt to alter the usage data 46 stored in the medical device 10. By doing so, the reprocessing entity may attempt to alter and overwrite the usage data 46.

The first and second authorized control units 250, 260 are authorized to write usage data 46 to the memory component 20. In one embodiment, the first level of access is full-write (write, erase, and/or re-write) access. The second level of access is write-once access. In other words, the method prevents the second authorized control unit 260 from writing data more than once to the memory component 20.

The third unauthorized control unit 270 is not authorized to write usage data 46, and therefore, has no write access to the memory component 20. In other words, the method prevents the third authorized control unit 270 from writing usage data to the memory component 20.

In one example, access of the control units 250, 260, 270 includes access to the medical device 10. In another example, access of the control units 250, 260, 270 includes access to the memory component 20 of the medical device 10, or the data structure 30 of the memory component 20. Additionally, access of the control units 250, 260, 270 may include access to write usage data 46 to the memory component 20 or data structure 30. In yet another example, access of the control units 250, 260, 270 may include the ability to read the encryption key 50 from the data structure 30.

The first level of access may be a highest level of access and the second level of access may be the lowest level of access. The third control unit 20 generally has no access to the memory component 20 or data structure 30.

Authorization of the control units 250, 260, 270 to write usage data 46 may be determined according to various methods. In one example, authorization is determined by checking the authenticity of the control units 250, 260, 270 and/or the medical device 10. Any suitable information relating to the control units 250, 260, 270 and/or medical device 10 may be checked to determine authenticity. For example, such data may relate to device configuration, type, manufacturer, version, calibration, compliance, date of manufacture, and the like. The medical device 10 may store data in the memory unit 20 to verify whether the attached control unit 250, 260, 270 is authentic. For example, such data may include the identification data stored in the unique data segment 66 in the data structure 30.

The first and second authorized control units 250, 260 have access to the encryption key 50 in the data segment 34 and, therefore, have access to write authentic usage data 46 to the memory component 20. In other words, the first or second authorized control units 250, 260 read the encryption key 50 from the data structure 30 and encrypt the usage data 46 with the encryption key 50 such that the usage data 46 remains authentic.

At step 202, the first authorized control unit 250 is permitted access to the encryption key 50 such that the first authorized control unit 250 is permitted to write the authentic usage data 46 to the memory component 20. The first authorized control unit 250 may access the encryption key 50 at any given time and write the authentic usage data 46 to the memory component 20 at any given time.

At step 204, the second authorized control unit 260 is permitted access to the encryption key 50 only once such that the second authorized control unit 260 is permitted write-once access to the memory component 20. Said differently, the second authorized control unit 260 initially gains access to the encryption key 50 to write the authentic usage data 46 to the memory component 20. However, as described in detail above, the encryption key 50 previously stored in the memory component 20 is subsequently eliminated, as shown in FIG. 8. In other words, the method includes eliminating the encryption key 50 from the data structure 30 such that the second authorized control unit 260 is no longer able to read the encryption key 50 from the medical device. As such, the second authorized control unit 260 can no longer access the encryption key 50. This prevents the second authorized control unit 260 from modifying the authentic encrypted usage data. Thus, the second authorized control unit 260 is limited to write-once access to the memory component 20. In other words, the second authorized control unit 260 is prohibited from subsequently modifying, e.g., overwriting, erasing, or changing, the encrypted usage data written to the memory component 20. In some instances, data segments 34 are encrypted a second time using asymmetric encryption where the encryption key 50 is only known to second authorized control unit 260.

The third unauthorized control unit 270 is prohibited access to the encryption key 50. As such, at step 206, the third unauthorized control unit 270 is prohibited from any write access to the memory component 20. In other words, the third unauthorized control unit 270 is not capable of writing authentic usage data 46.

As described above, the decryption key 60 provides decryption of the encrypted usage data such that the usage data 46 is comprehensible. As such, the decryption key 60 provides access to read the encrypted and authentic usage data 46 written to the memory component 20.

In one embodiment, all authorized control units have access to the decryption key 60. In other words, both the first and second authorized control units 250, 260 have access to the decryption key 60. By having access to the decryption key 60, the first and second authorized control units 250, 260 are permitted to decrypt and read the authentic usage data 46. For the second authorized control unit 260, the encrypted usage data may be repeatedly decrypted by the decryption key 50 thereby providing repeatable read access to the usage data 46 even when the associated encryption key 50 is eliminated.

The third unauthorized control unit 270 is prohibited access to the decryption key 60. As such, the third unauthorized control unit 270 is prohibited from any read access to the usage data 46.

In another embodiment, the first authorized control unit 250 is permitted access to the master encryption key 72. Access to the master encryption key 72 permits the ability to write valid hash data in the verification data segment 70. Access to the master encryption key 72 is provided only to the first authorized control unit 250. The second authorized control unit 260 and the third unauthorized control unit 270 are not permitted access to the master encryption key 72.

Similarly, the first authorized control unit 250 is permitted access to the master decryption key 74. As described, the master decryption key 74 permits decryption of, and read access to, the entire data structure 30. In one embodiment, access to the master decryption key 74 is provided only to the first authorized control unit 250. In other words, the second authorized control unit 260 and the third unauthorized control unit 270 are not permitted access to the master decryption key 74. As such, the second and third control units 260, 270 are not permitted to decrypt the hash data. In another embodiment, access to the master decryption key 74 is provided to both the first and second authorized control units 250, 260, but not to the third unauthorized control unit 270.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for manipulating a data structure provided on a memory component of a medical device, the medical device being connectable to a console, the data structure including an encryption key, a decryption key associated with the encryption key, and verification data to protect the decryption key, the method comprising:
   providing data related to operation of the medical device;
   reading the encryption key from the data structure;
   encrypting, at the console, the data with the read encryption key;
   storing the encrypted data on the data structure;
   eliminating the read encryption key from the data structure such that the read encryption key is no longer present on the memory component;
   reading, from the data structure, the decryption key associated with the read encryption key;
   decrypting the encrypted data with the read decryption key; and
   authenticating the decryption key with the verification data.

2. The method of claim 1 wherein decrypting the encrypted data is possible using only the decryption key associated with the encryption key that was used to encrypt the data.

3. The method of claim 1, further comprising randomly generating the encryption key and the decryption key such that the encryption key and the decryption key are unique to and exist solely for the medical device.

4. The method of claim 1, wherein the data structure includes a plurality of data segments and further comprising storing both the encryption key and the associated decryption key in single data segment.

5. The method of claim 1, wherein eliminating the read encryption key is further defined as overwriting the read encryption key with the encrypted data.

6. The method of claim 1, further comprising:
   storing in the data structure identification data related to identification of the medical device;
   protecting the identification data with the verification data; and
   authenticating the identification data with the verification data.

7. The method of claim 1, wherein the console further performs the steps of reading the encryption key, storing the encrypted data, eliminating the read encryption key, reading the decryption key, reading the encrypted data, decrypting the encrypted data, and authenticating the decryption key with the verification data.

8. The method of claim 1, wherein the data structure further comprises a plurality of encryption keys and a plurality of decryption keys, and with each one of the decryption keys being associated with one of the encryption keys.

9. The method of claim 8, wherein the data structure includes a plurality of data segments and further comprising:
   storing each one of the encryption keys in a different one of the data segments; and
   storing each one of the decryption keys in a different one of the data segments.

10. The method of claim 8, wherein the data structure includes a plurality of data segments and further comprising occupying all of the data segments with the encryption keys and the decryption keys.

11. The method of claim 8, further comprising randomly generating each of the encryption keys and each of the decryption keys such that the encryption keys are different from one another, the decryption keys are different from one another, and the encryption keys and the decryption keys are different from one another.

12. A medical device being connectable to a console, the medical device comprising:
   a memory component;
   a data structure stored on the memory component;
   an encryption key being stored in the data structure and being configured to be read from the memory component;
   a decryption key being stored in the data structure and being configured to be read from the memory component, and with the decryption key being associated with the encryption key;
   verification data to protect the decryption key; and
   encrypted data related to operation of the medical device being stored in the data structure and wherein the encrypted data is encrypted, at the console, by the encryption key that was previously stored in the data structure and subsequently eliminated such that the encryption key is no longer present in the memory component;
   wherein the decryption key associated with the eliminated encryption key is preserved on the memory component after elimination of the encryption key and wherein the decryption key is configured such that decrypting the encrypted data is possible using only the decryption key associated with the eliminated encryption key, and wherein the decryption key is authenticatable with the verification data.

13. The medical device of claim 12, wherein the encryption key and the decryption key are randomly generated such that the encryption key and the decryption key are unique to and exist solely for the medical device.

14. The medical device of claim 12, wherein the encrypted data is written over the encryption key to eliminate the encryption key.

15. The medical device of claim 12, wherein the data related to operation of the medical device comprises one or more of usage data and calibration data.

16. The medical device of claim 12, further comprising:
    identification data related to identification of the medical device being stored in the data structure;
    the verification data to further protect the identification data; and
    the identification data being authenticatable with the verification data.

17. The medical device of claim 12, wherein the medical device comprises a handpiece and wherein the memory component is positioned in the handpiece.

18. The medical device of claim 12, wherein the data structure further comprises a plurality of encryption keys and a plurality of decryption keys, and with each one of the decryption keys being associated with one of the encryption keys.

19. The medical device of claim 18, wherein the data structure includes a plurality of data segments and wherein each one of the encryption keys is stored in a different one of the data segments and wherein each one of the decryption keys is stored in a different one of the data segments.

20. The medical device of claim 18, wherein the data structure includes a plurality of data segments and wherein at least one encryption key and associated decryption key pair is stored in single data segment.

21. The medical device of claim 18, wherein each of the encryption keys and each of the decryption keys are randomly generated such that the encryption keys are different from one another, the decryption keys are different from one another, and the encryption keys and the decryption keys are different from one another.

22. A method of managing the ability of a console to modify authentic data on a memory component of a medical device that is connectable to the console, the memory component comprising a data structure including an encryption key, a decryption key associated with the encryption key, and verification data to protect the decryption key, the method comprising the console performing the steps of:
    reading the encryption key from the memory component of the medical device;
    encrypting, at the console, the data with the read encryption key such that the data remains authentic;
    storing the encrypted data on the data structure;
    eliminating the encryption key from the data structure such that the console is no longer able to read the read encryption key from the memory component of the medical device, thereby preventing the console from modifying the authentic data;
    reading, from the memory component, the decryption key associated with the read encryption key for providing the ability to read the authentic data;
    decrypting the encrypted data with the read decryption key; and
    authenticating the decryption key with the verification data.

23. The method of claim 22, wherein the memory component further includes identification data related to the medical device, the method further including protecting the decryption key and identification data using asymmetric key encryption providing a secret key and a public key.

24. The method of claim 23, further including providing one console access to the secret key and providing another console access to the public key.

25. The method of claim 22, further including protecting the encryption key and the authentic data using asymmetric key encryption utilizing a secret key and a public key.

26. The method of claim 25, further including providing one console access to the secret key and providing another console access to the public key.

27. The method of claim 22 wherein the memory component further includes identification data related to the medical device, and further comprising:
    protecting the identification data with the verification data; and
    authenticating the identification data with the verification data.

28. The method of claim 22, wherein the memory component further comprises a plurality of encryption keys and a plurality of decryption keys, and with each one of the decryption keys being associated with one of the encryption keys.

* * * * *